US009421296B2

(12) United States Patent
Hadba et al.

(10) Patent No.: US 9,421,296 B2
(45) Date of Patent: Aug. 23, 2016

(54) CROSSLINKED FIBERS AND METHOD OF MAKING SAME BY EXTRUSION (71) Applicants: SOFRADIM PRODUCTION, Trevoux (FR); COVIDIEN LP, Mansfield, MA (US)

(72) Inventors: Ahmad Robert Hadba, Middlefield, CT (US); Sebastien Ladet, Lyons (FR)

(73) Assignees: COVIDIEN LP, Mansfield, MA (US); SOFRADIM PRODUCTION, Trevoux (FR)

( * ) Notice: Subject to any disclaimer, the term of this patent is extended or adjusted under 35 U.S.C. 154(b) by 0 days.

(21) Appl. No.: 14/161,855

(22) Filed: Jan. 23, 2014

(65) Prior Publication Data

US 2014/0142626 A1 May 22, 2014

Related U.S. Application Data (62) Division of application No. 13/202,384, filed as application No. PCT/IB2010/000600 on Feb. 22, 2010, now Pat. No. 8,648,144.

(60) Provisional application No. 61/154,379, filed on Feb. 21, 2009.

(51) Int. Cl.
| | |
|---|---|
| *A61L 17/00* | (2006.01) |
| *D01F 6/60* | (2006.01) |
| *D01F 6/62* | (2006.01) |
| *D01F 6/80* | (2006.01) |
| *D01F 6/84* | (2006.01) |
| *D01F 6/04* | (2006.01) |
| *D01F 6/06* | (2006.01) |
| *D01F 6/30* | (2006.01) |
| *A61L 27/34* | (2006.01) |
| *A61L 29/08* | (2006.01) |
| *A61L 31/10* | (2006.01) |
| *D01F 2/00* | (2006.01) |
| *D01F 4/00* | (2006.01) |
| *D01F 6/00* | (2006.01) |
| *D01F 6/44* | (2006.01) |
| *D01F 6/88* | (2006.01) |
| *D01F 9/00* | (2006.01) |
| *B29C 47/00* | (2006.01) |

(52) U.S. Cl.
CPC .................. *A61L 17/00* (2013.01); *A61L 27/34* (2013.01); *A61L 29/085* (2013.01); *A61L 31/10* (2013.01); *B29C 47/0014* (2013.01); *D01F 2/00* (2013.01); *D01F 4/00* (2013.01); *D01F 6/00* (2013.01); *D01F 6/04* (2013.01); *D01F 6/06* (2013.01); *D01F 6/30* (2013.01); *D01F 6/44* (2013.01); *D01F 6/60* (2013.01); *D01F 6/62* (2013.01); *D01F 6/80* (2013.01); *D01F 6/84* (2013.01); *D01F 6/88* (2013.01); *D01F 9/00* (2013.01); *A61L 2400/18* (2013.01)

(58) Field of Classification Search
CPC ............. A61L 17/00; D01F 6/30; D01F 6/80; D01F 6/04; D01F 6/84; D01F 6/06; D01F 6/60; D01F 6/62; D01F 4/00; B29C 47/0014
USPC .............. 264/176.1, 177.1, 177.13, 186, 187, 264/178 F; 525/54.2, 54.21; 527/312
See application file for complete search history.

(56) References Cited

U.S. PATENT DOCUMENTS

| | | | |
|---|---|---|---|
| 3,767,085 A | 10/1973 | Cannon et al. | |
| 4,326,532 A | 4/1982 | Hammar | |
| 4,359,049 A | 11/1982 | Redl et al. | |
| 4,464,321 A | 8/1984 | Pittalis et al. | |
| 4,538,920 A | 9/1985 | Drake | |
| 4,753,536 A | 6/1988 | Spehar et al. | |
| 4,839,345 A | 6/1989 | Doi et al. | |
| 4,857,403 A | 8/1989 | De Lucca et al. | |
| 4,861,527 A | 8/1989 | DeLucca et al. | |
| 4,880,662 A | 11/1989 | Habrich et al. | |
| 5,021,207 A | 6/1991 | De Lucca et al. | |
| 5,372,585 A | 12/1994 | Tiefenbrun et al. | |
| 5,455,308 A | 10/1995 | Bastiaansen | |
| 5,562,946 A | 10/1996 | Fofonoff et al. | |
| 5,578,662 A | 11/1996 | Bennett et al. | |
| 5,582,955 A | 12/1996 | Keana et al. | |
| 5,612,050 A | 3/1997 | Rowe et al. | |
| 5,804,318 A | 9/1998 | Pinchuk et al. | |
| 5,911,942 A | 6/1999 | Fofonoff et al. | |
| 6,099,563 A | 8/2000 | Zhong | |
| 6,107,365 A | 8/2000 | Bertozzi et al. | |
| 6,107,453 A | 8/2000 | Zuccato et al. | |
| 6,312,725 B1 | 11/2001 | Wallace et al. | |

(Continued)

FOREIGN PATENT DOCUMENTS

| | | |
|---|---|---|
| BE | 1008260 A6 | 2/1996 |
| EP | 0490854 A2 | 6/1992 |

(Continued)

OTHER PUBLICATIONS

Fournier, D., et al.; Chemical Society Reviews, 2007, p. 1369-1380.*
Campos, L.M., et al.; Macromolecules, 2008, p. 7063-7070.*
Lee, S.H., et al.; Journal of Applied Polymer Science, 2004, vol. 92, p. 2054-2062.
Lutz, J.F.; Angewandte Chemie International Edition, published online Feb. 8, 2008, vol. 47, p. 2182-2184.
Q. Shi, et al., "The Immobilization of Proteins on Biodegradable Polymer Fibers via Click Chemistry", Biomaterials, 29, (2008), pp. 1118-1126.
Jerome, et al., "Recent Advances in the Synthesis of Aliphatic Polyesters Ring-Opening Polymerization", Advanced Drug Delivery Reviews, 60, (2008), pp. 1056-1076.

(Continued)

*Primary Examiner* — Robert Jones, Jr.

(57) ABSTRACT

The present disclosure relates to a method of forming fibers. First and second precursors, each possessing a core and at least one functional group known to have click reactivity, are mixed. The mixed precursors are then extruded under heat to cross-link during fiber production.

6 Claims, 3 Drawing Sheets

(56) References Cited

U.S. PATENT DOCUMENTS

| | | |
|---|---|---|
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,624,245 B2 | 9/2003 | Wallace et al. |
| 6,881,766 B2 | 4/2005 | Hain |
| 6,958,212 B1 | 10/2005 | Hubbell et al. |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |
| 7,667,012 B2 | 2/2010 | Saxon et al. |
| 7,795,355 B2 | 9/2010 | Matyjaszewski et al. |
| 7,807,619 B2 | 10/2010 | Bertozzi et al. |
| 7,981,444 B2 | 7/2011 | Tomalia et al. |
| 7,985,424 B2 | 7/2011 | Tomalia et al. |
| 8,034,396 B2 | 10/2011 | Kapiamba et al. |
| 8,648,144 B2 | 2/2014 | Hadba et al. |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0162903 A1 | 8/2003 | Day |
| 2003/0168756 A1* | 9/2003 | Balkus et al. ............... 264/10 |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |
| 2004/0185053 A1 | 9/2004 | Govindan |
| 2004/0209317 A1 | 10/2004 | Ting |
| 2004/0249438 A1 | 12/2004 | Lefranc et al. |
| 2005/0032081 A1 | 2/2005 | Ju et al. |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2005/0244453 A1 | 11/2005 | Stucke et al. |
| 2006/0018948 A1 | 1/2006 | Guire et al. |
| 2006/0036022 A1 | 2/2006 | Callaghan et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0142404 A1 | 6/2006 | Berge et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0212267 A1 | 9/2007 | Organ et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0021486 A1 | 1/2008 | Oyola et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0103564 A1 | 5/2008 | Burkinshaw et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2008/0317861 A1 | 12/2008 | Guan |
| 2009/0012457 A1 | 1/2009 | Childers et al. |
| 2009/0018646 A1 | 1/2009 | Zhao |
| 2009/0027603 A1 | 1/2009 | Samulski et al. |
| 2009/0038701 A1 | 2/2009 | Delmotte |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0099108 A1 | 4/2009 | Jones |
| 2009/0124534 A1 | 5/2009 | Reineke |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0203131 A1 | 8/2009 | Reineke et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2009/0325292 A1 | 12/2009 | Baker et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0104589 A1 | 4/2010 | Govindan et al. |
| 2010/0121022 A1 | 5/2010 | Musa et al. |
| 2010/0159508 A1 | 6/2010 | Yang et al. |
| 2010/0247433 A1 | 9/2010 | Tirrell et al. |
| 2010/0286405 A1 | 11/2010 | Fokin et al. |
| 2010/0291171 A1 | 11/2010 | Crescenzi et al. |

(56) References Cited

U.S. PATENT DOCUMENTS

| | | | |
|---|---|---|---|
| 2010/0303754 | A1 | 12/2010 | Turpin et al. |
| 2011/0008251 | A1 | 1/2011 | Chang et al. |
| 2011/0052696 | A1 | 3/2011 | Hult et al. |
| 2011/0060107 | A1 | 3/2011 | Matyjaszewski et al. |
| 2011/0143435 | A1 | 6/2011 | Stayton et al. |
| 2011/0177156 | A1 | 7/2011 | Szoka, Jr. et al. |
| 2011/0183417 | A1 | 7/2011 | Reineke |
| 2011/0213123 | A1 | 9/2011 | Bertozzi et al. |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 10/2008 |
| EP | 2014308 A2 | 1/2009 |
| EP | 2090592 A1 | 8/2009 |
| JP | 3294524 B2 | 6/2002 |
| WO | 2006012569 A1 | 2/2006 |
| WO | 2007041394 A2 | 4/2007 |
| WO | 2007121055 A1 | 10/2007 |
| WO | 2008013618 A1 | 1/2008 |
| WO | 2008075955 A2 | 6/2008 |
| WO | 2008077406 A2 | 7/2008 |
| WO | 2008108736 A1 | 9/2008 |
| WO | 2008115694 A2 | 9/2008 |
| WO | 2008120016 A1 | 10/2008 |
| WO | 2010095049 A1 | 8/2010 |

OTHER PUBLICATIONS

Zhang, et al., "2-Azido-2-deoxycellulose: .Synthesis and 1, 3-Dipolar Cycloaddition", Helvetica Chimica Acta, vol. 91, pp. 608-617 (2008).

R. Riva, et al., "Contribution of "Click Chemistry" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al. "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self.Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (.epsilon.-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoallcylidene Derivatives of 3-azido-3-deoxy-D-allose", Carbohydrate Research, 343, (2008), pp. 2118-2129. cited byapplicant.

Witczak et al., "A Click Chemistry Approach to Glycomimetics: Michael addition of 2,3,4,6-tetra-O-acetyl-1-thio-.beta.-D-glucopyranose to 4-deoxy-1,2-O-isopropylident-L-glycero-pent-4-enopyranos-3-ulose—a convenient route to novel4-deoxy-(1.fwdarw.5)-5-C-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of .beta.-cyclodextrin with oligoethyleneamines", Biomaterials, 30, (2009), pp. 928-938.

Arora, et al., "A Novel domino-click approach for the synthesis of sugar based unsymmetrical bis- 1,2,3-triazoles", Carbohydrate Research, 343, (2008), 139-144.

Chen, et al., "Synthesis of a C.sub.3-symmetric (1.fwdarw.6)-N-acetyl-.beta.-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, etal., "Effects of Trehalose Click Polymer Length on pDNA Complex Stability and Delivery Efficacy", Biomaterials, 28, (2007), pp. 2885-2898.

Godeau, et al., "Lipid-Conjugated Oligonucleotides via Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via i to i + 4 Intramolecular Side-chain to Side-chain Azide-Alkyne 1,3-Dipolar Cycloaddition" J. Org. Chem., 2008, 73 (15), pp. 5663-5614.

Dijk, et al., "Synthesis of Peptide-Based Polymers by Microwave-Assisted Cycloaddition Backbone Polymerization,"Biomacro molecules, 2007, 8(2), pp. 327-330.

Koster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. "Reactive polymer coatings that 'Click'.", Angewandte Chemie, International Edition 45, Apr. 2006, pp. 3360-3363.

(56) References Cited

OTHER PUBLICATIONS

Ossipov and Hilborn, "Poly(vinyl alcohol)-Based Hydrogels Formed by Click Chemistry", Macromelecules 2006, 39, pp. 1709-1718.
Binder and Sachsenhofer, "Click Chemistry in Polymer and Materials Science", Macromolecular Rapid Commun. 2007, 28, pp. 15-54.
International Search Report for PCT/IB10/000600 date of completion is Jul. 8, 2010 (4 pages).
Database WPI Week 199144 Thomson Scientific, London, GB; AN 1991-320678 XP002590920 &Jp 3213511 A (Toray Ind. Inc.) Sep. 18, 1991 (abstract).
Database WPI Week 200882 Thomson Scientific, London, GB; AN 2008-002390 XP002590921 &CN 101 260 570 A (Univ Donghua) Sep. 10, 2008 (abstract).

* cited by examiner

CROSSLINKED FIBERS AND METHOD OF MAKING SAME BY EXTRUSION

CROSS-REFERENCE TO RELATED APPLICATIONS

The present application is a divisional application of U.S. Ser. No. 13/202,384, filed Aug. 19, 2011, which is a U.S. National Stage Application filed under 35 U.S.C. §371(a) of International Application No. PCT/IB2010/000600 filed Feb. 22, 2010, which claims the benefit of and priority to U.S. Provisional Application Ser. No. 61/154,379 filed Feb. 21, 2009, the entire contents of which are incorporated by reference herein.

BACKGROUND

1. Technical Field

The present disclosure relates to crosslinked fibers, and more particularly to the use of click chemistry to form the crosslinked fibers, methods of preparing such fibers, and surgical devices made from such fibers.

2. Background of Related Art

Methods for making monofilaments that are suitable to fabricate surgical articles, such as sutures, generally include the steps of extruding at least one bioabsorbable or nonbioabsorbable polymer to provide filaments, drawing or stretching the solidified filaments to achieve molecular orientation, and annealing the drawn filaments to relieve internal stresses.

Various spinning methods may be employed, such as melt spinning, wet or dry solvent spinning, and reaction spinning. Melt spinning uses heat to melt the fiber polymer to a viscosity suitable for extrusion through the spinneret. Solvent spinning uses large amount of organic solvents to dissolve the fiber polymer into a fluid polymer solution suitable for extrusion through a spinneret. Reaction spinning involves the formation of filaments from prepolymers and monomers that are further polymerized and cross-linked after the filament is formed.

Click chemistry refers to a collection of reactions capable of forming a highly reliable molecular connection in solution or bulk state. Click chemistry reactions may be highly selective, high yield reactions which should not interfere with one another as well as other reactions.

It would be desirable to make filaments useful in making surgical devices by extruding a mixture containing first and second precursors functionalized for crosslinking by click chemistry and aided by the process controls of the spinning process, such as temperature, pressure, and time.

SUMMARY

A first aspect of the present invention is a method for forming fibers comprising:
obtaining a mixture by mixing first and second precursors each possessing a core and at least one functional group known to have click reactivity; and
extruding said mixture in order to crosslink the first and second precursors to produce a fiber.

In the present application, unless otherwise specified, the expressions 'functional group", "functional group known to have click reactivity" and "reactive member" are used interchangeably to designate a functional group known to have click reactivity.

In the present application, unless otherwise specified, the expression "functionalized polymer" or "functionalized precursor" means the polymer or the precursor possessing the functional group as defined herein.

Another aspect of the present invention is a fiber prepared by:
obtaining a mixture by mixing first and second precursors each possessing a core and at least one functional group known to have click reactivity; and
extruding said mixture in order to crosslink the first and second precursors to produce a fiber.

In embodiments, the first and second precursors are biocompatible polymers.

In embodiments, for each of said first and second precursors, the core comprises synthetic materials selected from poly(lactic acid), poly (glycolic acid), poly(lactide), poly(glycolide), poly(trimethylene carbonate), poly (dioxanone), poly (hydroxybutyrate), poly (phosphazine), polyesters, polyethylene terephthalate, ultra-high molecular weight polyethylene, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, poly (saccharides), polyamides, poly (iminocarbonates), polyalkylene oxalates, polyoxaesters, polyorthoesters, polyphosphazenes, biopolymers, polymer drugs and copolymers, block copolymers, homopolymers, blends and combinations thereof.

In embodiments, for each of said first and second precursors, the core comprises natural polymers selected from collagen, cellulose, poly (amino acids), polysaccharides, chitosan and chitosan derivatives (e.g., chitosan acetate/formate polymers), hyaluronic acid, gut, copolymers and combinations thereof.

In embodiments, for each of said first and second precursors, the functional group known to have click reactivity is selected from the group consisting in amine, sulfate, thiol, hydroxyl, azide, alkyne, alkene, and carboxyl groups.

In embodiments, the functional group of the first precursor is an azide and the functional group of the second precursor is an alkyne.

In embodiments, the functional group of the first precursor is a thiol and the functional group of the second precursor is an alkene.

In embodiments, the cores of said first and second precursors being selected from chitin and chitosan, the mixture is spun from anisotropic solution of chitin or chitosan.

In embodiments, the cores of said first and second precursors being collagen, the mixture is gel spun.

In embodiments, the functional group of the first precursor has click reactivity with the functional group of the second precursor.

A method for forming fibers includes mixing first and second precursors each possessing a core and at least one functional group known to have click reactivity and extruding the first and second precursors under heat to crosslink the first and second precursors to produce a cross-linked fiber.

Another aspect of the invention is a method for forming fibers comprising:
mixing first and second precursors each possessing a core and at least one functional group known to have click reactivity; and
extruding the first and second precursors to crosslink the first and second precursors to produce a fiber.

Another aspect of the invention is a fiber prepared by cross-linking a mixture of a first precursor and a second precursor during extrusion, the first precursor possessing at least one functional group and the second precursor possessing a functional group having click reactivity with the first functional group.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE EMBODIMENTS

Fibers in accordance with the present disclosure are prepared by spinning or extruding a mixture of first and second precursors each having at least one functional group known to have click reactivity. Cross-linked fibers formed in accordance with the present disclosure may be made by reaction of a functionalized first precursor with a functionalized second precursor under conditions which cause the two precursors to form covalent bonds without the use of a chemical crosslinking agent or catalyst. In this respect, process controls, such as temperature, time, and pressure will aid in the cross-linking of the precursors.

The first and second precursors may each possess a core functionalized with one or more reactive members.

The core of the first and second precursors may be the same or different and may be any suitable biocompatible material. Thus, the fibers may be prepared from any first and second precursors known to form biocompatible polymers. Each core may be a homopolymer or a copolymer, including random copolymer, block copolymer, or graft copolymer. In embodiments, the first and second precursors are different materials, thus forming copolymer filaments. Each core may be a linear polymer, a branched polymer, or a dendrimer. The core of the first and second precursors may be a natural material or a synthetic material and may be bioabsorbable or non-bioabsorbable. It should of course be understood that any combination of natural, synthetic, bioabsorbable and non-bioabsorbable materials may be used to form the fibers.

Some non-limiting examples of synthetic materials from which the core may be prepared include, but are not limited to polylactic acid), poly (glycolic acid), poly(lactide), poly(glycolide), poly(trimethylene carbonate), poly (dioxanone), poly (hydroxybutyrate), poly (phosphazine), polyesters, polyethylene terephtalate, ultra-high molecular weight polyethylene, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, poly (saccharides), polyamides, poly (iminocarbonates), polyalkylene oxalates, polyoxaesters, polyorthoesters, polyphosphazenes, biopolymers, polymer drugs and copolymers, block copolymers, homopolymers, blends and combinations thereof. Suitable natural polymers from which the core may be prepared include collagen, cellulose, poly (amino acids), polysaccharides, chitosan and chitosan derivatives (e.g., chitosan acetate/formate polymers), hyaluronic acid, gut, copolymers and combinations thereof.

In preparing fibers in accordance with the present disclosure, the first and second precursors may be commercially available pre-functionalized cores or may be synthesized.

With respect to each core, it is contemplated that a plurality of first reactive members may be present and that they may be terminally located, or alternatively located along the length of the polymer chain. In embodiments, the precursors have from about 2 to about 50 reactive members.

Examples of the types of reactions that are known to have click reactivity include cycloaddition reactions. Cycloaddition reactions can be used to form the fibers of the present disclosure. These reactions represent highly specific reactant pairs that have a chemoselective nature, meaning that they mainly react with each other and not other functional groups. One example of a cycloaddition reaction is the Huisgen 1,3-dipolar cycloaddition of a dipolarophile with a 1,3 dipolar component that produce five membered (hertero)cycles. Examples of dipolarophiles are alkenes, alkynes, and molecules that possess related heteroatom functional groups, such as carbonyls and nitriles. Specifically, another example is the 2+3 cycloaddition of alkyl azides and acetylenes. Other cycloaddition reactions include Diels-Alder reactions of a conjugated diene and a dienophile (such as an alkyne or alkene).

Other examples of the types of reactions that are known to have click reactivity include a hydrosilation reaction of H—Si and simple non-activated vinyl compounds, urethane formation from alcohols and isocyanates, Menshutkin reactions of tertiary amines with alkyl iodides or alkyl trifluoromethanesulfonates, Michael additions, e.g., the very efficient maleimide-thiol reaction, atom transfer radical addition reactions between —SO2Cl and an olefin ($R^1$, $R^2$—C=C—$R^3$, $R^4$), metathesis, Staudinger reaction of phosphines with alkyl azides, oxidative coupling of thiols, many of the procedures already used in dendrimer synthesis, especially in a convergent approach, which require high selectivity and rates, nucleophilic substitution, especially of small strained rings like epoxy and aziridine compounds, carbonyl chemistry like formation of ureas, and addition reactions to carbon-carbon double bonds like dihydroxylation. Therefore, attached functionality may be chosen from acetylene bond, an azido-group, a nitrile group, acetylenic, amino group, phosphino group. The click chemistry reaction may results in the addition of a functional group selected from amino, primary amino, hydroxyl, sulfonate, benzotriazole, bromide, chloride, chloroformate, trimethylsilane, phosphonium bromide or bio-responsive functional group including polypeptides, proteins and nucleic acids, to the polymer.

Thus, suitable reactive members that may be applied to the core include, for example, an amine, sulfate, thiol, hydroxyl, azide, alkyne, alkene, and carboxyl groups. The reactive member may be a thiol. Alternatively, the reactive member may be an azide. Alternatively, the reactive member may be an alkyne. Alternatively, the reactive member may be an alkene.

The core of the first and second precursor can be provided with click reactive members using any variety of suitable chemical processes.

For example, the monomers from which the core is made can be functionalized so that the reactive members appear along the length of the core. In such embodiments, monomers can be initially functionalized with a group such as a halogen to provide a reactive site at which the desired first click reactive member can be attached after polymerization. Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with a click reactive member, for example, by converting pendant chlorides on the core into azides by reaction with sodium azide. See, R. Riva et al., *Polymer* 49 pages 2023-2028 (2008) for a description of such reaction schemes. Other methods for functionalizing lactones are described in Jerome et al., *Advanced Drug Delivery Reviews*, 60, pages 1056-1076 (2008) and Shi et al., *Biomaterials*, 29, pages 1118-1126 (2008). The entire disclosure of each of these three articles is incorporated herein by this reference.

Where one of the precursors includes a core that is an amino-containing material (e.g., collagen, polypeptide, glycosaminoglycan, etc.), the core of the second precursor can be functionalized by using any method known to those skilled in the art to provide pendant portions of the core with moieties which are capable of covalently bonding with the amino groups on the first precursor. Examples of such pendant moieties, corresponding to the functional groups as defined herein, include aldehyde groups, sulfone groups, vinylsulfone groups, isocyanate groups, acid anhydride groups, epoxide groups, aziridine groups and episulfide groups. In addition, electrophilic groups such as —CO$_2$N(COCH$_2$)$_2$, —CO$_2$N(COCH$_2$)$_2$, —CO$_2$H, —CHO, —CHOCH$_2$, —N═C═O, —SO$_2$CH═CH$_2$, —N(COCH)$_2$, —S—S—(C$_5$H$_4$N) may also be added to pendant chains of the core to allow covalent bonding to occur with the any cores showing amino group on their chains. Other suitable functional groups which may be added to the core include groups of the following structures wherein X is Halogen and R is hydrogen or C$_1$ to C$_4$ alkyl:

Those skilled in the art reading this disclosure will readily envision chemical reactions for activating other core materials to render them suitable for use as precursors in the presently described methods.

The first and second precursors may take the form of any solution, suspension, semi-solid, or solid material capable of allowing the two components to interact and crosslink during extrusion. The first and second precursors may be in granular, pellet, or powder form, or alternatively, may be in a dilute solution. Suitable solvents which may be utilized to form a dilute solution include any biocompatible solvent within the purview of those skilled in the art which will not interfere with the reaction of the reactive members of the first and second precursors. Suitable solvents which may be utilized include, for example, polar solvents such as water, ethanol, triethylene glycol, dimethyl sulfoxide, glymes (such as diglyme, triglyme, tetraglyme, and the like), polyethylene glycols, methoxy-polyethylene glycols, dimethylformamide, dimethylacetamide, gamma-butyrolactone, n-methylpyrrolidone, ketones such as methyl ethyl ketone, cyclohexanone, diethylene glycol momethyl ether acetate, diethylene glycol monobutyl ether acetate, diethylene glycol monomethyl ether, diethylene glycol monoethyl ether, diethylene glycol monobutyl ether, diethylene glycol monoisobutyl either, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution. The amount of solvent used will depend on a number of factors, including the particular first precursor, second precursor, or combination thereof that are to be employed and the intended end use of the composition.

The first and second precursors may be placed in a hopper and mixed thoroughly to provide substantially uniform distribution of the first precursor among the second precursor. The first and second precursors may be mixed using any conventional technique, with or without heating. For example, a mechanical mixer, a static mixer, or combinations thereof, may be employed to assist in providing a substantially uniform distribution of first and second precursors. After mixing, the mixture is extruded or spun to form one or more filaments or fibers.

The rate of cross-linking of the first and second precursors of the present disclosure may be tailored by controlling the concentration of the first precursor and the second precursor. Generally, a faster cross-link time may be observed at a higher concentration of either the first or second precursors than the rate observed for the same components at a lower concentration. In embodiments, the ratio of first precursor reactive members to second precursor reactive members is from about 1:2 to about 1:1.

Figure 1:
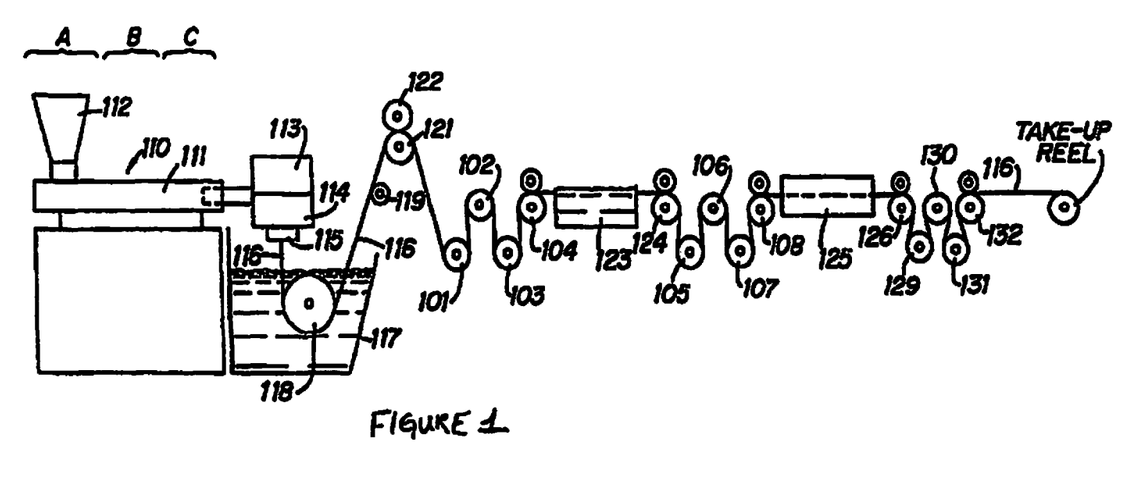
FIG. 1 is a schematic illustration of an apparatus which is suitable for carrying out a fiber manufacturing process in accordance with the present disclosure.

Known spinning apparatuses can be used for the production of filaments, in accordance with the present disclosure. FIG. 1 schematically illustrates a filament manufacturing operation in accordance with the disclosure. Extruder unit 110 is of a known or conventional types and is equipped with controls for regulating the temperature of barrel 111 in various zones thereof, e.g., progressively higher temperatures in three consecutive zones, A, B, and C along the length of the barrel. The first and second precursors to be spun into filaments are introduced to the extruder through hopper 112. Prior to or during placement in hopper 112, the first precursor is combined with the second precursor and mixed in a one-pot process. Adding heat during the mixing and/or extruding steps aids in the curing time of the first and second precursors, as faster curing rates are observed at higher temperatures.

Motor-driven metering pump 113 delivers the melt extruded first and second precursor mixture at a constant rate and with high pressure to spin pack 114 and thereafter through spinneret 115 possessing one or more orifices of desired diameter to provide a molten monofilament 116 which then enters quench bath 117, e.g., containing water, where the monofilament solidifies. The distance monofilament 116 travels after emerging from spinneret 115 to the point where it enters quench bath 117, i.e., the air gap, can vary. If desired, a chimney (not shown), or shield, can be provided to isolate monofilament 116 from contact with air currents which might otherwise affect the cooling of the monofilament in an unpredictable manner. In general, barrel zone A of the extruder can be maintained at a temperature of from about 100° C. to 220° C., zone B at from about 160° C. to 230° C. and zone C at from about 170° C. to about 240° C. Additional temperature parameters include: metering pump block 113 at from about 170° C. to about 230° C., spin pack 114 at from about 170° C. to about 230° C., spinneret 115 at from about 170° C. to about 230° C. and quench bath at from about 10° C. to about 80° C.

Monofilament 116 is passed through quench bath 117 around driven roller 118 and over idle roller 119. Optionally, a wiper (not shown) may remove excess water from the monofilament as it is removed from quench bath 117. On exiting the quench bath the monofilament is wrapped around a first godet 121 provided with nip roll 122 to prevent slippage which might otherwise result from the subsequent stretching operation; and subsequently wrapped around godets 101, 102, 103 and 104 or any other suitable godet arrangement. Monofilament 116 passing from godet 104 is stretched, e.g., with stretch ratios on the order of from about 3:1 to about 10:1 and preferably from about 4:1 to about 7:1, to effect its orientation and thereby increase its tensile strength.

In the stretching operation, monofilament 116 may be drawn through hot water (or other suitable liquid medium) draw bath 123 by means of godets 124, 105, 106, 107 and 108 or any other suitable arrangement of godets which rotate at a higher speed than godet 104 to provide the desired stretch ratio. The temperature of hot water draw bath 123 is advantageously from about 30° C. to about 90° C. and preferably is from about 30° C. to about 50° C. In an alternative stretching operation, generally preferred for smaller sutures sizes, e.g., sizes 3/0 to 8/0, monofilament 116 may be drawn by godets 124, 105, 106, 107, and 108 or any other suitable godet arrangement through hot air convection oven chamber 123 at a temperature of from about 30° C. to about 140° C., and preferably from about 50° C. to about 130° C. to provide the desired amount of stretch.

Following the stretching operation, monofilament 116 optionally may be subjected to an on-line annealing and/or additional stretching without shrinkage or relaxation with shrinkage operation as a result of which the monofilament shrinks. In the process of FIG. 1, on-line annealing with or without relaxation when desired is accomplished by driving monofilament 116 by godets 126, 129, 130, 131, and 132 or any other suitable godet arrangement through second hot air oven chamber 125 at a temperature of from about 40° C. to about 150° C., and preferably from about 60° C. to about 130° C. During the relaxation process, at these temperatures, monofilament 116 will generally recover to within about 80 to about 97 percent, and preferably to within about 95 percent, of its pre-annealed length to provide the finished suture. For relaxation, the third godet rotates at a slower speed than the second godet thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 60° C. to about 130° C. After a suitable period of residency in the heating cabinet, e.g., about 18 hours or so, the suture will have undergone essentially no shrinkage. Variables such as the annealing temperatures, time, and pressure may affect the curing time of the fibers as well. The creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures are then ready to be packaged and sterilized.

In embodiments, cross-linked fibers from chitin or chitin derivative cores that have been functionalized with click reactive members can be produced according to the present disclosure by spinning from anisotropic solution. Suitable methods for solution spinning chitin or chitin derivative fibers in general are disclosed in European Patent Nos. EP0328050A2 and EP0077098A2, the entire disclosures of which are incorporated herein by this reference. Such fibers can have tensile properties which typically fall between 4-8 g/d tenacity and 150-250 g/d initial modulus.

High strength chitosan fibers can be prepared by spinning an anisotropic solution of chitosan or a derivative of chitin or chitosan through an inert gas and into a coagulating bath, removing the as-spun fiber and treating it with alkali to remove N-acetyl, O-acetyl or other pendant groups at the 2, 3 and 6 carbon positions of the glucosamine repeating unit. Treatment of fibers is by immersion of the fibers into a solution of NaOH. With fine denier fibers, e.g., 4-5 dpf., a 5 minute immersion at 70° C. in a 50% wt. solution of NaOH is satisfactory. A 2-3 hr. exposure at 80° C. in a 30% wt. solution is useful with chitosan acetate formate fiber. With chitosan acetate, temperatures in the range of 80° to 116° C. at NaOH concentration of 30% have been found useful with the higher temperatures requiring less time for completion of the reaction. Severe treatments are generally to be avoided since they may cause excessive interfilament fusion and a product of inferior quality. Conversion of the starting fiber to a chitosan fiber is confirmed if the chitosan fiber is readily soluble in dilute (3-20% wt.) acetic acid.

Figure 2:
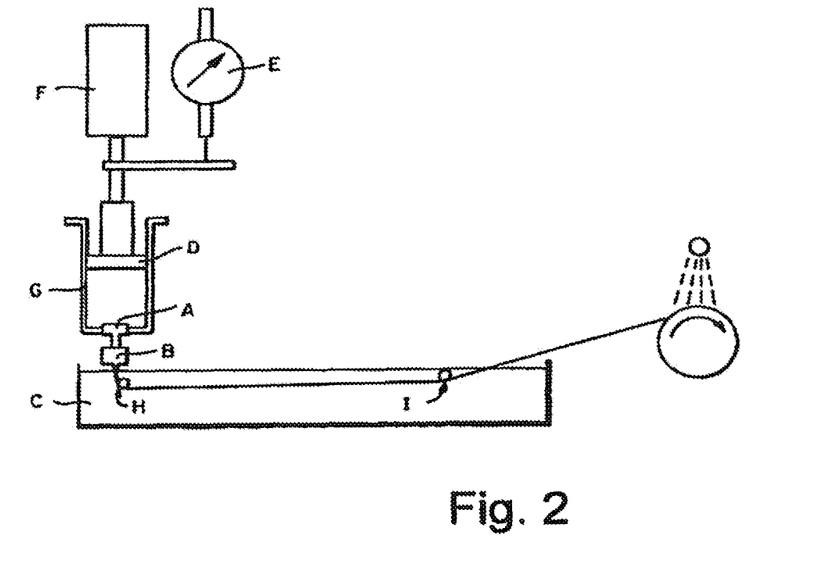
FIG. 2 is a schematic illustration of another apparatus which is suitable for carrying out a fiber manufacturing process in accordance with the present disclosure.

In using the apparatus of FIG. 2 an anisotropic solution of chitin or a chitin derivative is placed in spin cell (G). A piston (D) activated by hydraulic press (F) and associated with piston travel indicator (E) is positioned over the surface of the solution, excess air is expelled from the top of the cell and the cell is sealed. The spin cell is fitted at the bottom with the following screens (A) for solution filtration: four to six 325-mesh screens. The filtered solution is then passed into a spinneret pack (B) containing two or three 325-mesh screens. Solutions are extruded through an air gap at a controlled rate into a static bath (C) using a metering pump to supply pressure at piston (D). The fiber is passed around a pin (H), pulled through the bath, passed under a second pin (I) and wound onto a bobbin. The air gap between the spinneret face and the coagulation bath is typically 0.6 to 2.0 cm. The coagulation bath temperature is generally held below 100° C.

Figure 3:
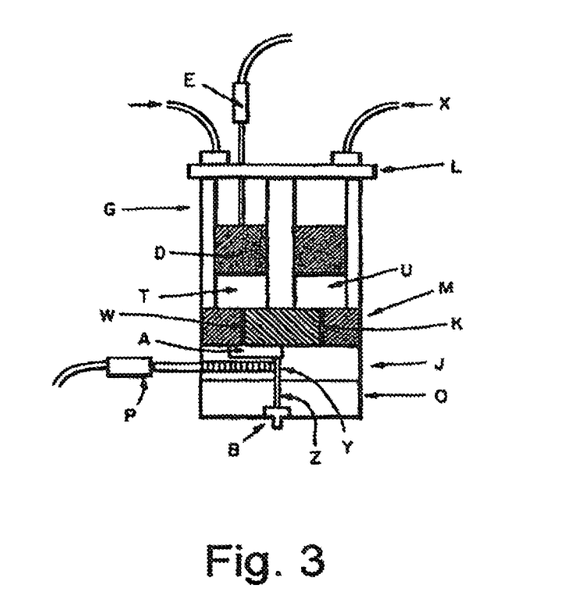
FIG. 3 is a cross-sectional view of yet another embodiment of a fiber manufacturing process.

In using the apparatus of FIG. 3, filter plate (J) is replaced by mixing plate (R). Polymer dope is placed in cylinder bore (T) and then piston (D) and cap plate (L) is fitted to the spin cell (G). A driver fluid (e.g. water) is pumped into the upper part of bore (T) through feed line (F). The piston (D) is displaced by the driver fluid, thereby pushing the polymer dope through passages (W), (S) in mixing plate (R) and then through passage (K) in distribution plate (M) into second cylinder bore (U). This process is then reversed by pumping fluid through feed line (X). The aforementioned forward and reverse process is repeated several times to effect a mixing of the polymer dope. Component (E) acts to sense the position of cylinder (D).

After mixing is complete (about 30 cycles), mixing plate (R) is replaced by filter plate (J) and polymer dope is extruded from bore (T) through passage (W), through filter pack (A) containing 2 Dutch Twill Weave 165×800 mesh screens, through passage (Y) in filter plate (J) and passage (Z) in spinneret mounting plate (O) and out of spin cell (O) through spinneret (B). The extruded dope is spun into a bath and taken up as described for FIG. 2. Pressure of the polymer dope during spinning is measured by pressure transducer (P).

In other embodiments, cross-linked fibers from collagen or collagen derivative cores that have been functionalized with click reactive members can be produced according to the present disclosure by gel spinning. Suitable methods for gel spinning collagen fibers in general are disclosed in U.S. Pat. Nos. 5,562,946 and 5,911,942, the entire disclosures of which are incorporated herein by this reference.

Figure 4:
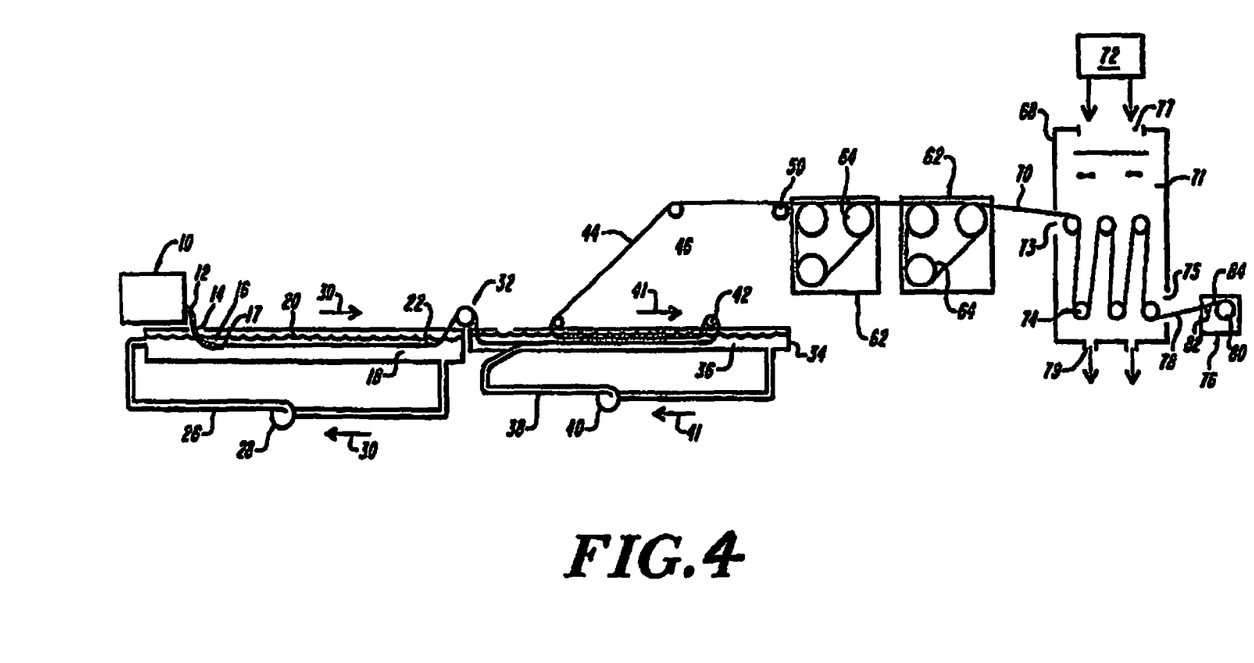
FIG. 4 is a schematic illustration of another apparatus suitable for spinning fiber in accordance with the present disclosure.

In an illustrative apparatus for gel spinning such fibers shown in FIG. 4, collagen reservoir chamber 10 holds a liquid collagen solution. In one embodiment, a suitable chamber is a stainless steel syringe. Reservoir tube 12 is attached to collagen reservoir chamber 10 for directing collagen solution from collagen reservoir chamber 10 through infusion pump 14 to spinneret 16. Infusion pump 14 is capable of raising the pressure of the collagen material such that it can be extruded through spinneret nozzle 17 of spinneret 16. In embodiments, a positive displacement metering pump is used. Spinneret 16 can be single bore or multiple bore to produce monofilament or multifilament fibers respectively. The spinneret bores can be of various diameters or have tapered profiles to form fibers of different sizes and tensile strengths. Co-component fibers can be produced with other specialized spinnerets as are known in the art. In one embodiment, spinneret nozzle 17 has diameters in the range of between about 100 and 1,000 microns.

Coagulation bath 18 has a coagulation solution 20 that can cause the liquid collagen to form a collagen gel, such as a 0.75% alkaline alginic acid in a boric acid buffer or sugar solutions or polyethylene glycol solution which also has hydrophilic properties. The opening of spinneret is immersed in a flowing coagulation solution 20. Coagulation bath 18 is suitably sized for allowing extrusion of fiber from spinneret 16 through coagulation solution 20 while having a sufficient residency time for collagen gel fiber 22 to form. Coagulation bath 18 can be heated and instrumented for monitoring the relevant process variables, such as temperature, pH and velocity. Coagulation bath 18 allows collagen gel fiber 22 to be formed in a horizontal trough or in a tube or vertically in a tube. Coagulation bath 18 is configured to allow circulation of coagulation solution 20 through recirculating loop 26 by circulating pump 28. Coagulation bath flow can be in the same direction 30 of fiber travel. At the end of the coagulation bath 18, roller 32 is for directing fiber out of the coagulation bath. Roller 32 is motorized and can be activated to wind collagen gel fiber 22 and subsequently tow collagen gel fiber 22 at desired speeds.

Dehydrating bath 34 is adjacent to roller 32 and coagulation bath 18 and is configured to allow fiber 22 to be drawn into dehydrating bath 34 from roller 32. Dehydrating bath 34 holds dehydrating solution 36, such as 90% ethanol, which allows further dehydration and annealing of the fiber and promotes polymerization of the collagen to improve fiber strength. An example of another suitable dehydration solution composition is acetone. Dehydrating bath 34 is configured to allow variable circulation of dehydrating solution 36 through recirculating loop 38 by circulating pump 40 which can be adjusted directionally, such as direction 41 or in the opposite direction. Return rollers 42, which can be near each end of dehydrating bath 34, allow the fiber path to be lengthened by doubling back to make any number of multiple passes through dehydrating bath 34 to allow further dehydration and promote polymerization of the collagen.

Partially dehydrated fiber 44 is wound around roller 46 to second roller 50 and then to stretching roller means 62, wherein the fiber can undergo a controlled deformation by being stretched between two groups of rollers 64 rotating at slightly different rates of speed. The speed of rotation of rollers 64 can be precisely controlled with digital microprocessors arranged in a closed feedback loop. The fibers are wrapped around each roller 64 several times to prevent fiber slippage relative to the roller surfaces. Roller 64 surfaces can made of a polymer or a hardened metal resistant to corrosion. Roller 64 rotations can be adjusted individually to allow the fiber to be stretched beyond the elastic yield point to produce a longer fiber of reduced diameter. Stretching roller means 62 can operate under semi-dry or dry conditions and also under high moisture content atmosphere.

Drying cabinet 68 has opening 73 for receiving stretched fiber 70 from stretching rollers 62. Drying cabinet 68 has passage 71 through drying cabinet 68 for receiving warm, dry filtered air or a dry inert gas, such as dry nitrogen gas, from gas source 72 at a suitable temperature and humidity for drying stretched fiber 70. The air can be passed through air passage opening 77 into passage 71 and exiting from air passage opening 79. In embodiments, the temperature of the air is between about 35° C. and 39° C. The humidity is in the range of between 10 and 20 percent relative humidity. Drying cabinet 68 has a series of rollers 74 which allows stretched fiber 70 to remain in drying cabinet 68 while being rolled, thereby increasing the residence time of fiber 70 in drying cabinet 68. Drying cabinet rollers 74 are adjustable in distance between each other and to compensate for the fiber line speed. Drying cabinet rollers 74 can be driven at a surface roller speed that can be synchronized with that of stretching roller means 62. Drying cabinet 68 has a door to provide access to the rollers for threading the leader thread.

Take-up winder 76 is for receiving dried fiber 78 from exit 75 of drying cabinet 68. Take-up winder 76 has spool 80 for receiving dried fiber on a removable spindle bobbin. Take-up winder 76 has a slip clutch 82 to provide a constant fiber line tension and fiber line speed as the spooled fiber rotates radially around spool 80. Fiber spool 80 can wind the fiber level or by randomly winding with the take-up winder 76.

Fibers formed in accordance with the present invention may be used for a variety of surgical and wound applications. The fibers, for example, may be used alone, such as for example, for closing wounds and incisions in the form of monofilament or multifilament sutures. Multifilament sutures may be constructed using any technique within the purview of those skilled in the art, such as spinning and braiding the fibers together. The fibers may also be used in combination with the other absorbable or non-absorbable fibers to form multifilament sutures or to form knitted, woven, or non-woven meshes or fabrics. A wide variety of surgical articles can be manufactured from the fibers of the present disclosure. These include but are not limited to sutures as discussed above, threads, rods, filaments, yarns, meshes, slings, patches, wound dressings, drug delivery devices, fasteners, and other implants and composite materials, such as pledgets, buttresses, adhesion barriers, and the like.

The fibers may further be use for delivery of a bioactive agent. Thus, in some embodiments, at least one bioactive agent may be combined with either the first precursor or the second precursor and/or may be separately applied to finished fiber. The agents may be freely admixed with the precursors (making sure not reactive with them) or may be tethered to the precursors through any variety of chemical bonds. In these embodiments, the present fibers can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present fiber in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent in the bioactive coating of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the coating composition applied in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-vitals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Devices formed with the fibers of the present disclosure, such as a mesh, may be at least partially coated with a bioresorbable coating by a surface treatment for enhanced properties. For example, the coating may be collagen, chitosan, polysaccharides, or mixtures thereof. The polysaccharides may be hyaluronic acid, alginic acid, polyglucuronic acid, chitosan, starch, soluble cellulose derivatives, and mixtures thereof. Such a coating makes it possible to eliminate crevices which may form during the construction and interplay of the fibers where bacteria or inflammatory cells may develop, thus making it possible to reduce the risk of inflammation and sepsis by preventing the installation of undesirable bacteria and/or microorganisms and/or inflammatory cells into the filled or covered crevices.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:
1. A fiber prepared by:
obtaining a mixture by mixing first and second precursors each possessing a core and at least one functional group known to have click reactivity, for each of the first and second precursors, the core comprises the same synthetic material and the functional group known to have click reactivity is selected from the group consisting of thiol, azide, alkyne, and alkene, groups, wherein the synthetic material is selected from polyethylene terephthalate, ultra-high molecular weight polyethylene, polypropylene, polyamide, and copolymers, block copolymers, homopolymers, blends and combinations thereof; and
extruding said mixture in order to crosslink the first and second precursors without use of chemical crosslinking agent or catalyst to produce a fiber.

2. The fiber of claim 1, wherein the functional group of the first precursor is an azide and the functional group of the second precursor is an alkyne.

3. The fiber of claim 1, wherein the functional group of the first precursor is a thiol and the functional group of the second precursor is an alkene.

4. A fiber prepared by:
   obtaining a mixture by mixing first and second precursors each possessing a core and at least one functional group known to have click reactivity, the core of said first and second precursors including collagen and the functional group known to have click reactivity is selected from the group consisting of thiol, azide, alkyne, and alkene groups; and
   gel-spinning said mixture in order to crosslink the first and second precursors to produce a fiber, wherein the functional group of the first precursor has click reactivity with the functional group of the second precursor to crosslink the first and second precursors without use of chemical crosslinking agent or catalyst.

5. The fiber of claim 4, wherein the functional group of the first precursor is an azide and the functional group of the second precursor is an alkyne.

6. The fiber of claim 4, wherein the functional group of the first precursor is a thiol and the functional group of the second precursor is an alkene.

* * * * *